United States Patent [19]

Nicolas et al.

[11] Patent Number: 5,226,939
[45] Date of Patent: Jul. 13, 1993

[54] SURGICAL SMOKE EVACUATION SYSTEM

[75] Inventors: Ed F. Nicolas, Moreno Valley; Ian M. Williamson, Redondo Beach, both of Calif.

[73] Assignee: Stackhouse, Inc., Riverside, Calif.

[21] Appl. No.: 780,768

[22] Filed: Oct. 22, 1991

[51] Int. Cl.⁵ .............................................. B01D 46/42
[52] U.S. Cl. ........................................ 55/309; 55/467; 55/276
[58] Field of Search .................. 55/309, 387, 276, 467

[56] References Cited

U.S. PATENT DOCUMENTS

| | | | |
|---|---|---|---|
| 2,096,484 | 10/1937 | Farmer | 55/313 |
| 2,565,764 | 8/1951 | Flanagan | 55/309 |
| 3,736,927 | 6/1973 | Misaqi | 128/145.6 |
| 4,019,508 | 4/1977 | Der Estephanian | 128/142.7 |
| 4,055,173 | 10/1977 | Knab | 128/139 |
| 4,549,542 | 10/1985 | Chien | 128/201.24 |
| 4,781,021 | 11/1988 | Winberg | 55/276 |
| 4,810,269 | 3/1989 | Stackhouse et al. | 55/276 |
| 4,900,344 | 2/1990 | Lansing | 55/322 |
| 4,963,134 | 10/1990 | Backscheider | 604/319 |
| 4,986,839 | 1/1991 | Wertz | 55/274 |
| 5,047,072 | 9/1991 | Wertz et al. | 55/387 |

Primary Examiner—Bernard Nozick
Attorney, Agent, or Firm—Richard L. Myers

[57] ABSTRACT

A surgical air vacuum apparatus includes an air pump disposed in a primary air channel for moving air between an inlet port and an outlet port of the vacuum. The air pump has properties for generating heat while moving the air, and the moving air has characteristics for cooling the pump. An air filter disposed in the primary channel has a tendency to block the air that would otherwise cool the air pump. Means is provided for combining a secondary air channel and the primary air channel along at least one passage to introduce bleed air to the pump when the filter blocks the primary channel.

17 Claims, 3 Drawing Sheets

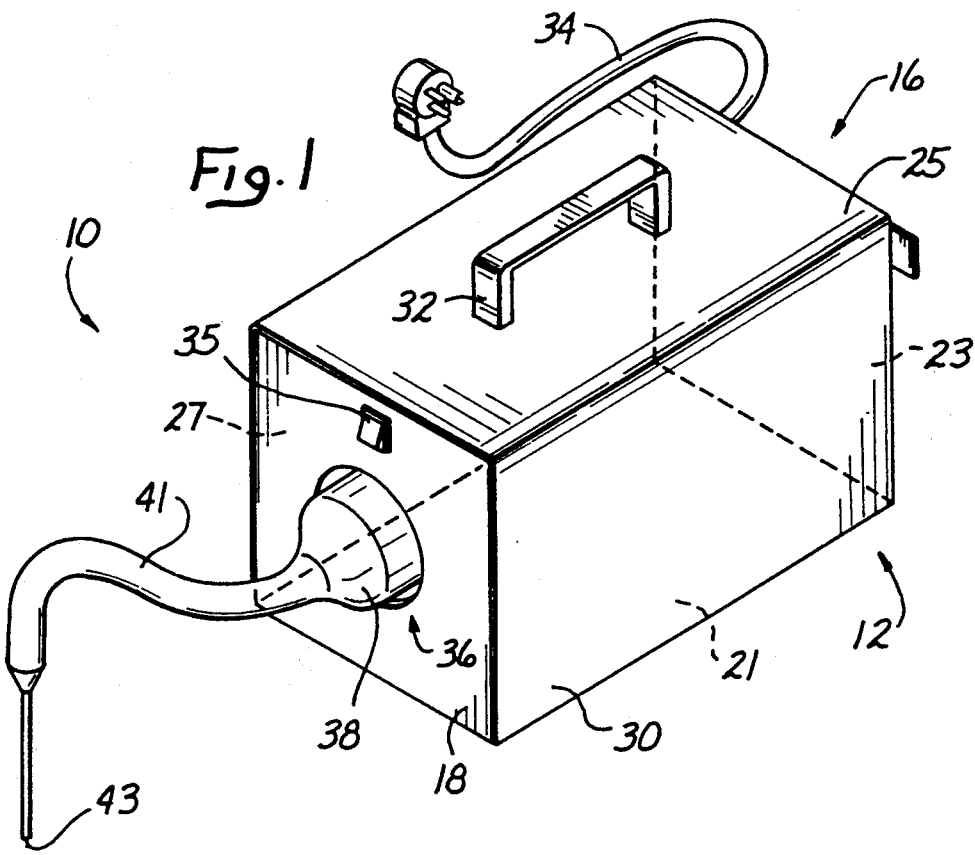
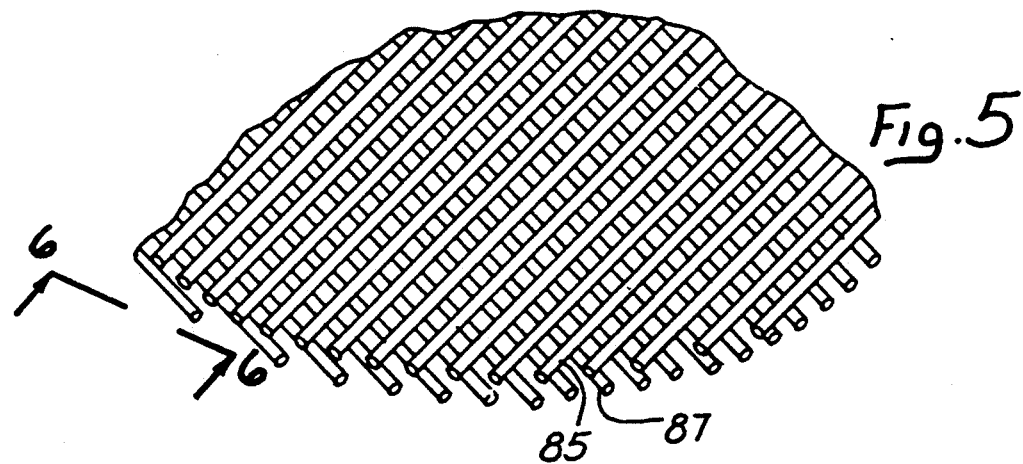
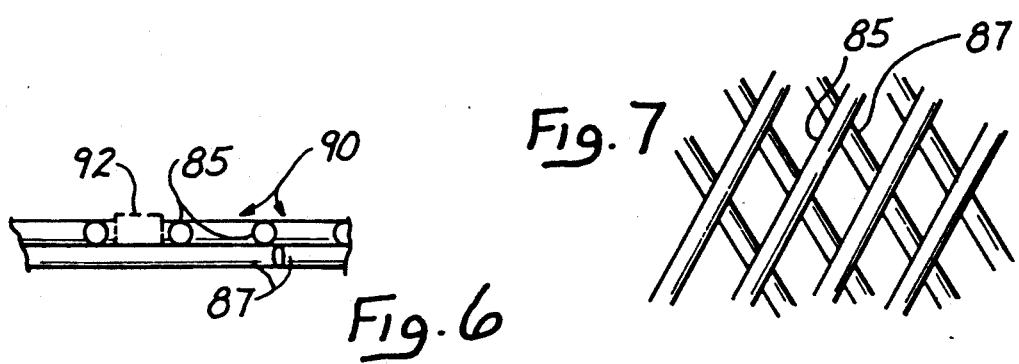

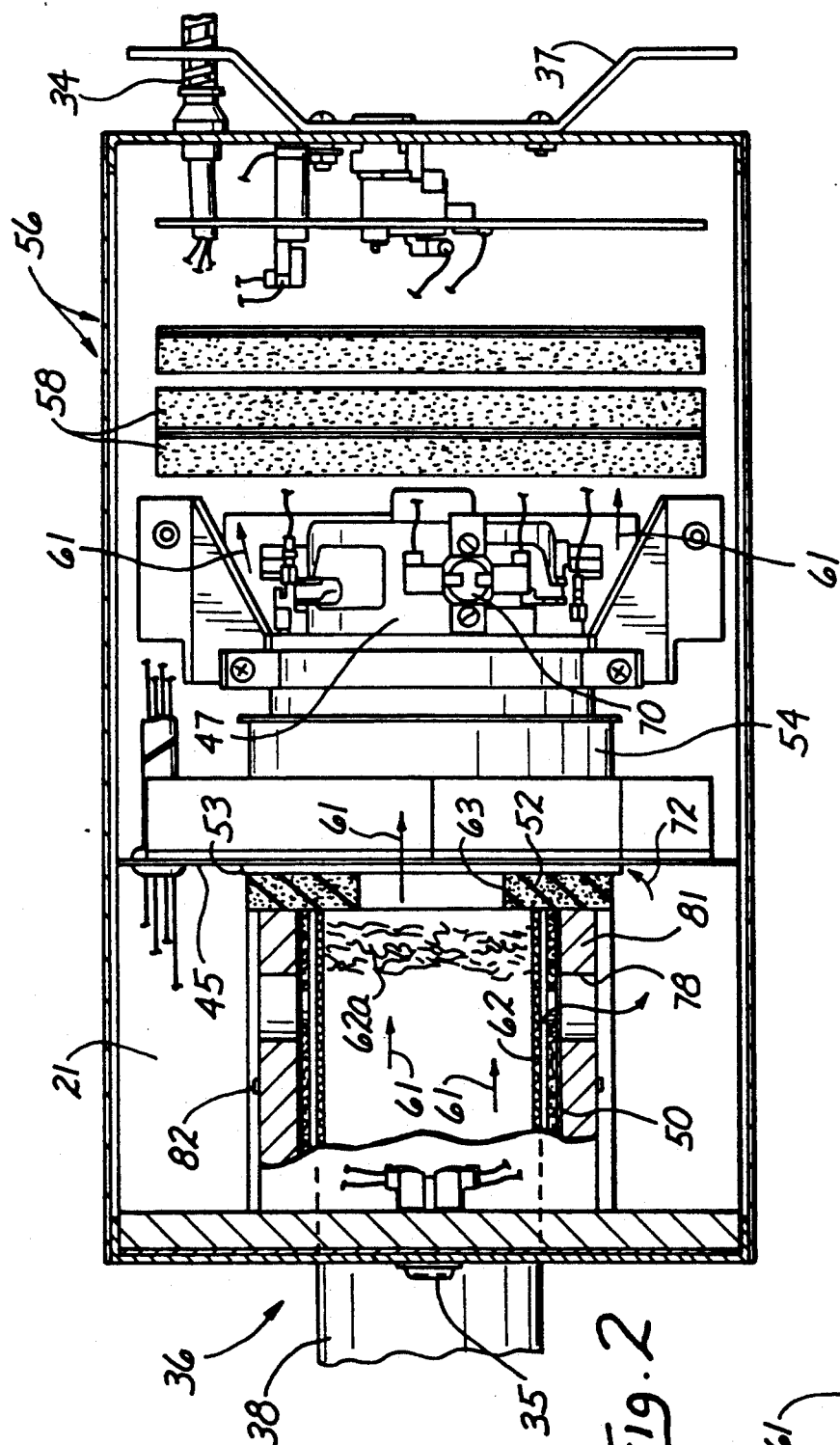
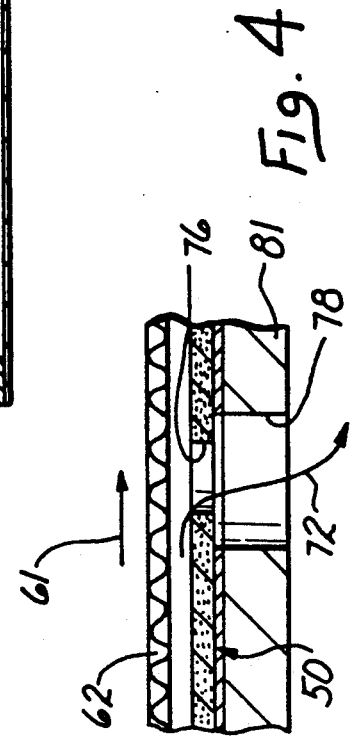
Fig. 2
Fig. 4

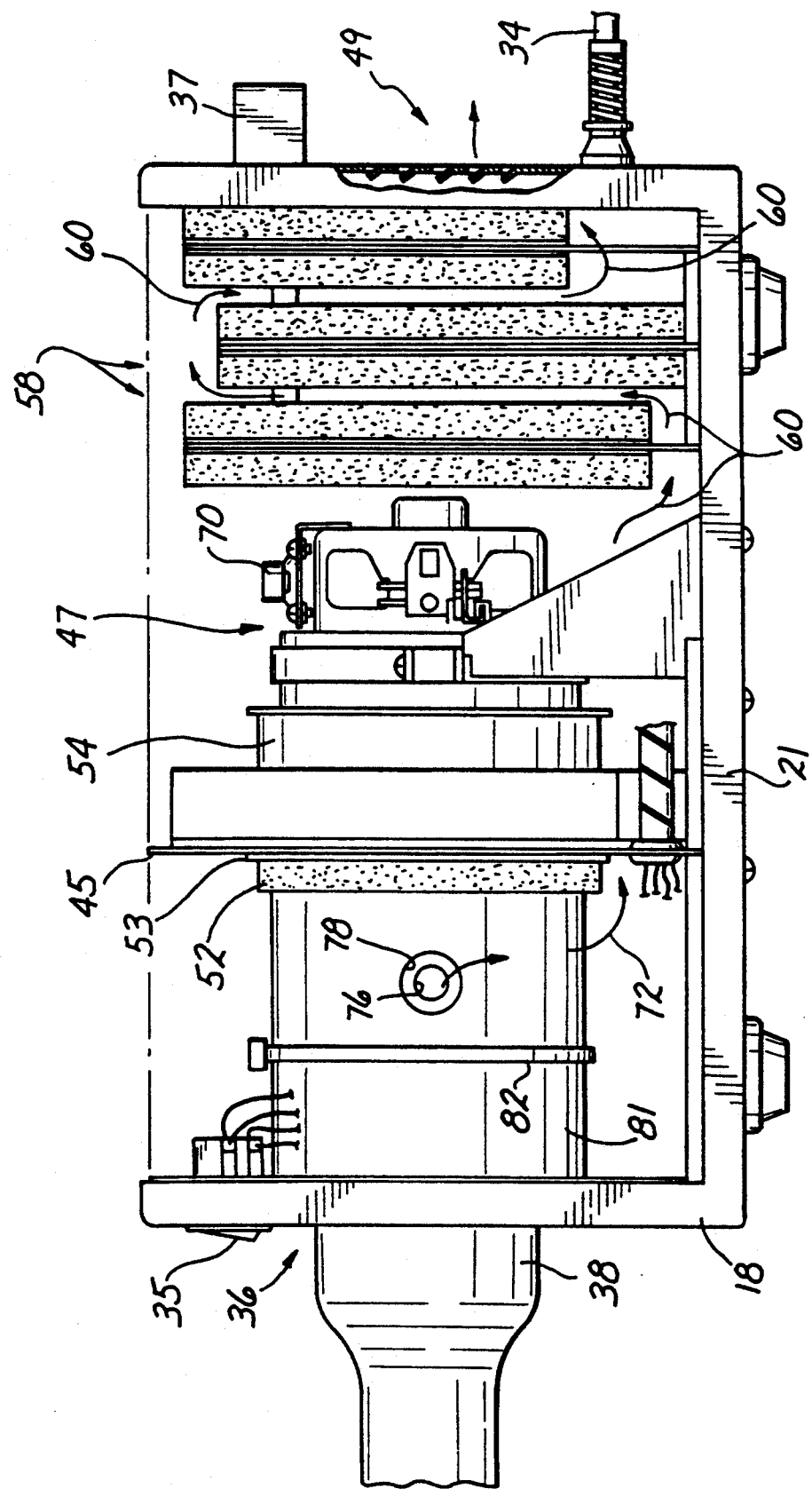

SURGICAL SMOKE EVACUATION SYSTEM

BACKGROUND OF THE INVENTION

1. Field of the Invention

This invention relates generally to vacuum apparatus and more specifically to surgical smoke evacuators and filters.

2. Discussion of the Prior Art

Lasers and electrosurgical apparatus are becoming increasingly popular for performing surgical operations. These devices are used both for cutting and cauterization of tissue. These devices are particularly advantageous for their precise cutting and the reduced bleeding which typically results. Unfortunately, as these devices vaporize the tissue they tend to create a large quantity of surgical smoke which at best is noxious and at worst may include dangerous micro-organisms and toxic chemicals.

Various vacuum apparatus have been designed for use in an operating room. These devices tend to be large since they include multiple filters and are designed for use over an extended period of time.

As doctors and surgeons become more comfortable with use of the modern lasers and electrosurgical devices, their use is moving from the operating room into the doctors, office for out-patient care. The removal of warts and cancerous tissue is often addressed by these devices in a doctor's office.

When surgery is performed in a doctor's office as opposed to the operating room of a hospital, the requirements for a vacuum apparatus change. First, the doctor's office is relatively small and cannot be encumbered by a large vacuum/filter. Second, the surgeries tend to be relatively small in size and short in duration. For example, it may take less than 5 minutes to remove a wart using an electrosurgical device. Also, since the surgery is relatively small, the quantity of smoke tends to be considerably less. As a result, smaller filters having a cumulative run time of less than 20 minutes can be accommodated. All of these requirements suggests that a smaller smoke evacuator is not only possible, but is desirable.

SUMMARY OF THE INVENTION

In accordance with the present invention, a small vacuum/filter is provided with a greatly reduced size while still maintaining the capacity to evacuate and filter surgical smoke associated with smaller operations. In a preferred embodiment the evacuator includes an enclosure having an inlet port and an outlet port and a primary air flow channel extending therebetween. A motor or air pump is provided to generate this air flow but in the process it also creates heat. Normally the air flow through the primary channel will cool the motor but if that flow becomes even partially blocked, the motor may not receive sufficient cooling. For this reason a secondary air flow channel is provided to introduce bleed air to the motor which is sufficient to meet its cooling requirements.

The structure includes a filter housing which communicates with the inlet port and a labyrinth of baffles which provide sound control near the outlet port. A disposable filter inserted in the filter housing forms part of the primary channel. The secondary air flow channel includes a circumferential air passage which exists between the air filter and its housing. A hole in the housing directs the secondary air flow outwardly of the filter housing.

A bleed air mesh is provided to receive the bleed air from outside the filter housing and to introduce it into the primary air channel for cooling the motor. Importantly, this bleed air mesh is non-woven and has a generally planar configuration so that it adds little to the overall size of the evacuator.

In one aspect of the invention, a surgical air vacuum has an air pump disposed in a primary air channel for moving air between an inlet port and an outlet port. The pump has properties for generating heat while moving the air, and the moving air has characteristics for cooling the pump. A filter, which cleans the air moving through the primary channel, has a tendency to accumulate material which blocks the air that would otherwise flow through the filter to cool the pump. A secondary air channel extends from a secondary port to an intersection of the primary channel and the secondary channel. A combining means having a generally planar configuration is disposed generally transverse to the primary channel at the intersection. Portions of the combining means form at least one passage disposed along the secondary channel for conduction bleed air into the pump to cool the pump when the filter blocks the primary channel.

In another aspect of the invention, a surgical air vacuum includes an enclosure and a partition connected to the enclosure next to an air pump which moves air between inlet and outlet ports. The pump has properties for generating heat while moving the air and the moving air has characteristics for cooling the pump. A filter disposed in the primary channel between the inlet port and the partition filters the air moving through the primary channel but has a tendency to block air that would otherwise flow through the filter to cool the pump. Means defining a secondary air channel is provided for conducting bleed air to the pump when the primary channel is blocked. This defining means includes a plurality of passages extending along the secondary channel and intersecting the primary channel between the inlet port and the pump means.

These and other features and advantages of the invention will become more apparent with the description of preferred embodiments and reference to the associated drawings.

DESCRIPTION OF THE DRAWINGS

FIG. 1 is a perspective view of an enclosure filter and inlet tube associated with one embodiment of the present invention;

FIG. 2 is a top plan view of the evacuator with a cover removed;

FIG. 3 is a side-elevation view of the evacuator with the cover removed;

FIG. 4 is an enlarged cross-sectional view of the bleed air channel illustrated in FIG. 2;

FIG. 5 is a perspective view of a bleed air mesh associated with the present invention;

FIG. 6 is a side-elevational view of the mesh taken along lines 6—6 of FIG. 5; and FIG. 7 is a top plan view of the mesh of FIG. 5.

DESCRIPTION OF PREFERRED EMBODIMENTS

A vacuum/filter apparatus is illustrated in FIG. 1 and referred to generally as an evacuator 10. A preferred embodiment of this apparatus is particularly adapted for the evacuation and filtration of surgical smoke. Such smoke is typically developed when electrosurgical apparatus and lasers are used for cutting and cauterizing. The evacuator 10 is relatively small in size and light in weight to enhance its portability. This makes it particularly desirable for use in small rooms, such as doctor's offices, and particularly easy to store when not in use.

In the illustrated embodiment, the evacuator 10 includes an enclosure 12 which is formed from a base assembly and an overlying cover assembly 16. The base assembly 14 includes a front panel 18 as well as a base frame 21 and rear panel 23 which are best shown in FIG. 2. The cover assembly 16 includes a top 25 and downwardly extending side panels 27 and 30. A handle 32 facilitates carrying of the evacuator 10 when the cover assembly 16 is attached to the base assembly 14.

A power cord 34 enters the rear panel 23 and provides suitable electrical power, such as 110 volt ac to the evacuator 10. A power switch 35 is provided on the front panel 18 to energize the evacuator 10. A bracket 37 can be attached to the rear panel 23 to facilitate wrapping the cord 34 in a confined configuration thereby enhancing the portability of the evacuator 10.

An inlet port 36 is also provided in the front panel 18 and is configured to receive a front loaded filter 38. An inlet hose 41 is, typically provided for connection to the filter 38 and extension to the operative site which is originating the surgical smoke. The hose 41 may have a length such as six feet and an internal diameter such as ⅜ inch. At the distal end of the hose 41, a two foot section of quarter inch tubing may be added to facilitate desirable orientation of a suction tip 43.

Interiorly of the evacuator 10, an upstanding partition 45 is fixed to the base frame 21 and provides a support for an air pump motor 47. The motor 47 is positioned to facilitate air flow through a primary air channel extending from the inlet port 36 to an outlet port 49, best shown in FIG. 3. The outlet port 49 in a preferred embodiment consists of a plurality of louvers which facilitates the exhausting of filtered air from the evacuator 10.

Between the ports 36 and 49, a primary air flow channel extends though a filter housing 50, a seal 52 and a mesh 53 which is of particular interest to the present invention. The primary channel extends rearwardly of the mesh 53 through an impeller housing 54, and the motor 47. Between the motor 47 and the outlet port 50, a series of baffles 56 are provided in the form of a torturous path defined by sheets of foam 58. The baffles 56 are oriented in the conventional manner to direct air flow along the surface of the foam sheets 58 as illustrated generally by the arrows 60 in FIG. 3. These baffles 56 not only enhance the filter characteristics of the evacuator 10 but also greatly reduce the sound associated with its operation. In the illustrated embodiment, the primary channel is designated generally by the arrows 61.

In a preferred embodiment the filter 38 is specially configured for receipt through the port 36 into the filter housing 50. The filter 38 has a case 62, which is generally cylindrical in shape. At its forward end, the case 62 tapers conically to a friction fit which is configured to receive the distal end of inlet hose 41. At its rearward end, the case 62 of the filter 38 is open. When the filter 38 is operatively inserted horizontally through the port 36, the open end at the rearward end of the filter 38 seats against the seal 52. This seal 52 has a generally toroidal configuration which defines a hole 63 along the primary channel 61.

In a preferred embodiment, the filter case 62 encloses an Ultra Low Penetration Air (ULPA) filter material 62a capable of filtering 99.999% of particles greater than 0.1 micron in size. The filter material may also include charcoal which tends to adsorb noxious odors. Although the filter 38 is much smaller than those associated with operating room evacuators, it nevertheless has a cumulative run time of approximately 20 minutes which is deemed to be sufficient for outpatient surgery.

The motor 47 is energized by electrical power from the power cord 34 which is interrupted by the on/off switch 35. When the filter 38 is inserted through the inlet port 36, operation of the motor brings the rear end of the filter case 62 into sealing engagement with the foam 52. An impeller (not shown) in the housing 54 creates a vacuum drawing air through the inlet hose 41, the filter 38, the hole 63 in the mesh 53. This air in the primary channel is cleaned by the filter 38 and quieted by the baffles 56 before it is exhausted through the outlet port 50. In a preferred embodiment the motor 47 creates a vacuum equivalent to 64 inches of water with a flow of 68 cubic feet per minute without load. When the load is applied, this flow drops to 3 cubic feet per minute. Operation of the motor 47 under load creates considerable heat which, under normal conditions, is dissipated by air flowing through the primary channel. For purposes of safety, a thermostatic cut-out 70 can be provided to interrupt power to the motor 47 at an elevated temperature such as 235° F.

As an alternative to driving the motor 47 to an overheated condition, provision is made in the present invention for bleed air to cool the motor when the primary air flow channel is clogged or blocked. This typically occurs when the filter 38 becomes blocked by filtered particles.

This bleed air can be introduced into the evacuator 10 through any port extending to the outside. In a preferred embodiment the bleed air flows through a secondary channel illustrated by the arrows 72. This secondary channel begins at the inlet port 36 and passes circumferentially of the filter 38 between the filter housing 50 and the inside of the case 62. The bleed air exits this circumferential space thorough a hole 76 in the housing 50 and a hole 78 in silencing insulation 81 which surround the housing 50. This insulation 81 can be held in place around the filter housing 50 by a strap 82.

In a preferred embodiment, the inside diameter of the housing 50 is 3.250 inches, and the outside diameter of the filter case 62 is 3.125 inches. It follows that the circumferential space between the filter 38 and the housing 50 which defines the initial portion of the secondary channel 72 has a radial dimension of 0.0625 or 1/16 inch. As the bleed air passes through the hole 78 in the insulation 81, it moves into the large interior space defined by the enclosure 12. From this location, the bleed air enters the primary channel 61 forwardly of the motor 47. In this manner, the bleed air passes through the motor 47 to facilitate the dissipation of heat. In a preferred embodiment, the bleed air enters the primary channel 61 by way of the mesh 53.

In the mesh 53 the secondary channel 72 is characterized by a non-woven structure consisting of a first plurality of parallel fibers 85 which are individually attached to a second plurality of parallel fibers 87. Since the mesh 53 is non-woven, both the fibers 85 and 87 are straight and extend in respective parallel planes.

The fibers 85 extend at a particular angle, such as 60°, with respect to the fibers 87. Since one of the purposes of the second fibers 87 is to maintain the first fibers 85 in their generally parallel relationship, it may be desirable to maximize the points of contact between the fibers 85 and 87.

With this configuration, the mesh 53 defines a plurality of passages 90 which have a cross-sectional configuration similar to the dotted rectangle 92 illustrated in FIG. 6. These passages 90 extend generally parallel to each other between adjacent pairs of the fibers 85. With the fibers 85 defining the passages 90, the cross fibers 87 function primarily to hold the passage fibers 85 in a separated parallel relationship.

The mesh 53 is representative of any structure which combines the first channel 61 and the secondary channel 72 at an intersection which precedes the motor 47. Although this combining means is provided int eh form of a non-woven mesh in the illustrated embodiment, it will be apparent that it can take other shapes indifferent embodiments. For example, the mesh may comprise a woven structure which would provide more torturous paths for the passages 90. In general, it has been found that a structure providing multiple passages 90 is preferred over a structure providing only a single passage. It is also suggested that generally straight passages 90 are preferred to reduce the noise level of the evacuator 10.

In a preferred embodiment, the mesh 53 is formed of a polypropylene polycarbonate material. The fibers 85, 87 have a diameter of about 0.040 inches so that the total thickness of the mesh 53 is approximately 0.080 inches. Both the fibers 85 and the fibers 87 are separated by a distance of 0.032 inches. It follows that the cross-sectional dimensions of the passages 90, the dimensions of the rectangle 92, are approximately 0.040 inches by 0.132 inches. This mesh 53 is manufactured and marketed under the trademark Naltex by Nalle Plastics, Inc. of Austin, Tex.

This particular mesh 53 is of advantage to the present invention because of its narrow thickness, and the multiplicity of passages which it provides at the intersection of the primary channel 61 and secondary channel 72. Providing a single hole at this intersection could increase air velocity, thereby dramatically increasing the noise associated with the flow of air. The multiplicity of passages greatly reduces this noise level in the evacuator 10. Thus the mesh 53 contributes greatly to the objectives of the evacuator 10, namely small size and quiet operation. The mesh 53 also facilitates assembly of the evacuator 10 since it is merely sandwiched between the foam seal 52 and the partition 45 which supports the motor 47.

Given the foregoing criteria, this miniature evacuator 10 is particularly adapted for use in small spaces such as a doctor's office. Of course it will be apparent that these criteria can be modified in other embodiments to accomplish the same objectives. For example, the mesh 53 can be configured with many different sizes and fiber orientations. The bleed air can be introduced into the enclosure 12 along many different channels. Alternative channels may not begin at the inlet port 36 and may not extent circumferentially in the space between the housing 50 and the filter 38. With the wide variety of variations available within this concept, one should not attempt to restrict the invention merely to those embodiments which are illustrated and disclosed but should ascertain the scope of the invention only with reference to the following claims.

We claim:

1. A surgical air vacuum apparatus comprising:
   an enclosure defining an inlet port and an outlet port;
   a primary air channel disposed between the inlet port and the outlet port;
   air pump means disposed in the primary air channel and including air moving means for moving air between the inlet port and the outlet port, and drive means connected to the air moving means for driving the air moving means, the drive means having properties for generating heat while driving the air moving means, the moving air having characteristics for cooling the drive means;
   filter means disposed in the primary air channel between the inlet port and the air moving means, for filtering the air moving through the primary channel, the filter means having a tendency to accumulate material filtered through the air and to block the air which would otherwise flow through the filter means to cool the drive means;
   a secondary port in the enclosure for receiving bleed air from outside the enclosure;
   a secondary air channel extending from the secondary port to an intersection of the primary channel and the secondary channel, the intersection being located between the filter means and the air pump means;
   means for combining the primary channel and the secondary channel at the intersection, the combining means having a generally planar configuration and being disposed substantially transverse to the primary channel; and
   portions of the combining means forming at least one passage disposed along the secondary channel for conducting the bleed air into the air pump means to cool the drive means when the filter blocks the primary channel.

2. The surgical air vacuum apparatus of claim 1 wherein the secondary port is disposed in juxtaposition to the inlet port.

3. The surgical air vacuum apparatus of claim 1 wherein the filter means includes:
   a filter housing having an interior surface with a first diameter, the interior surface defining at least a portion of the primary channel between the inlet port and the intersection;
   a filter disposed in the filter housing and having an exterior surface with a second diameter less than the first diameter; and
   the secondary channel being defined at least in part between the interior diameter of the filter housing and the exterior diameter of the filter.

4. The surgical air vacuum apparatus of claim 1 wherein the combining means forms a plurality of passages along the secondary channel to abate noise associated with the flow of the bleed air.

5. The surgical air vacuum apparatus of claim 1 wherein the combining means comprises a mesh.

6. The surgical air vacuum apparatus recited in claim 5 wherein the mesh is non-woven.

7. The surgical air vacuum apparatus recited in claim 6 wherein the mesh comprises:
   a plurality of fibers extending generally parallel to each other along the secondary channel and providing the passages with a generally rectangular cross-sectional configuration characterized by a length and a width; and each of the fibers having a particular diameter generally equivalent to the width of an adjacent one of the passages.

8. The surgical air vacuum apparatus recited in claim 7 wherein the mesh further comprises means for maintaining the fibers in a generally parallel, equally spaced relationship.

9. The surgical air vacuum apparatus recited in claim 8 wherein the fibers are first fibers and the maintaining means comprises a plurality of second fibers extending generally parallel to each other at a particular angle to the first fibers, the second fibers being connected to the first fibers to maintain the first fibers in the generally parallel, equally spaced relationship.

10. The surgical air vacuum apparatus recited in claim 9 wherein the mesh has a thickness not greater than twice the particular diameter of the first fibers.

11. The surgical air vacuum apparatus recited in claim 9 wherein the particular angle is other than 90°.

12. The surgical air vacuum apparatus recited in claim 1 wherein the particular angle is in a range between 40° and 80°.

13. The surgical air vacuum apparatus recited in claim 12 wherein the particular angle is about 60°.

14. The surgical air vacuum apparatus recited in claim 9 wherein the filter means includes a filter housing disposed between inlet and the partition and having walls with an inside diameter;

a filter adapted to be disposed in the filter housing and having an outside diameter less than the inside diameter of the walls; and the secondary channel extending through the walls of the filter housing.

15. The surgical air vacuum apparatus recited in claim 14 wherein the secondary port is disposed circumferentially of the inlet port.

16. The surgical air vacuum apparatus recited in claim 15 wherein the secondary channel is defined in part by the outside diameter of the filter and the inside diameter of the housing.

17. A surgical air vacuum apparatus comprising:

an enclosure defining an inlet port and an outlet port;

a primary air channel disposed between the inlet port and the outlet port;

an internal partition connected to the enclosure;

air pump means disposed in the primary air channel and in juxtaposition to the partition, the air pump means including air moving means for moving air between the inlet port and the outlet port along the primary channel, and drive means connected to the air moving means for driving the air moving means, the drive means having properties for generating heat while driving the air moving means, the moving air having characteristics for cooling the drive means;

filter means disposed in the primary air channel between the inlet port and the air moving means, for filtering the air moving through the primary channel, the filter means having a tendency to accumulate material filtered through the air and to block the air which would otherwise flow through the filter means to cool the drive means;

a secondary port in the enclosure for receiving bleed air from outside the enclosure;

means defining a secondary channel for conducting bleed air from the secondary port to the air pump means when the primary channel is blocked; and means disposed between the filter means and the partition for defining a plurality of passages extending along the secondary channel and intersecting the primary channel between the inlet port and the air pump means.

* * * * *